(12) United States Patent
Choe

(10) Patent No.: US 7,255,443 B2
(45) Date of Patent: Aug. 14, 2007

(54) QUANTITATIVE ANALYSIS APPARATUS FOR PHENOMENA OF GLARE AND THE METHOD FOR THE SAME

(76) Inventor: Chul Myung Choe, Olympic Sunsuchon A.P.T. 242-802, Oryun-Dong, Songpa-Ku (KR) 138-787

( * ) Notice: Subject to any disclaimer, the term of this patent is extended or adjusted under 35 U.S.C. 154(b) by 822 days.

(21) Appl. No.: 10/477,441

(22) PCT Filed: Mar. 5, 2002

(86) PCT No.: PCT/KR02/00379

§ 371 (c)(1),
(2), (4) Date: Nov. 7, 2003

(87) PCT Pub. No.: WO03/073923

PCT Pub. Date: Sep. 12, 2003

(65) Prior Publication Data

US 2005/0099598 A1    May 12, 2005

(51) Int. Cl.
*A61B 3/02* (2006.01)
(52) U.S. Cl. .................... 351/237; 351/246
(58) Field of Classification Search .......... 351/237, 351/246, 239, 238, 222
See application file for complete search history.

(56) References Cited

U.S. PATENT DOCUMENTS 4,405,216 A * 9/1983 Nadler et al. ............... 351/237
5,892,570 A * 4/1999 Stevens ..................... 351/237
5,946,075 A * 8/1999 Horn ......................... 351/246

FOREIGN PATENT DOCUMENTS

WO    WO 99/25239        5/1999
WO    WO 2000/32086 A1   10/2001

OTHER PUBLICATIONS

Fan-Paul, M.D., Nancy I. et al.; "Night Vision Disturbances After Corneal Refractive Surgery"; *Survey of Opthalmology*, vol. 47, No. 6, Nov.-Dec. 2002.
Stephenson, Christopher G., et al.; "Photorefractive Keratectomy"; *Ophthalmology*, vol. 105, No. 2, Feb. 1998.
Florakis, George J., M.D., et al.; "Night Vision Testing in Unoperated Eyes"; Journal of Refractive Surgery, vol. 12, Feb. 1996.

* cited by examiner

*Primary Examiner*—Hung Xuan Dang
(74) *Attorney, Agent, or Firm*—Jones Day

(57) ABSTRACT

The present invention is directed to a quantitatively analysis method for the phenomena of glare. The method includes the steps of reading light source picture information from a memory part and displaying the light source picture on a display part, reading position information of the circumference of the glare when a patient suffering from the phenomena of glare draws circumference line of the glare by means of a pointing device and calculating area of circumference of glare and outputting the calculated area. The output of the area indicates the condition of illness and the degree of remedy of the patient.

18 Claims, 3 Drawing Sheets

QUANTITATIVE ANALYSIS APPARATUS FOR PHENOMENA OF GLARE AND THE METHOD FOR THE SAME

FIELD OF THE INVENTION

The present invention relates to a quantitative analysis apparatus for phenomena of glare and the method for the same. By the present invention, it is possible for an ophthalmologist to quantitatively analyze a condition of the illness and the degree of remedy of a patient suffering from phenomena of glare.

BACKGROUND

The phenomena of glare or halo occurs when, after an operation of refraction-correction such as lasik or lasek, an iris of an eye excessively contracts and a pupil is enlarged that external light comes in through wider area than the operated cornea area. In this case, a focus of an image of objects is formed in front of a retina and the patient feels the glare or halo spread out from the object when he or she sees the objects. FIG. 1 shows the structure of an eye 100 in which the phenomena of the glare occurs. The operation of refraction-correction such as lasik or lasek is to cut off a portion of the cornea by means of laser in order to adjust the refractive index so that the object image is exactly focused on the retina. With reference to FIG. 1, by the operation, the cornea is cut off by the area of the shaded portion 23 so that the object focus f1 is exactly formed on the retina 40. Since the external light comes in through the cut off area of retina to pass lens 30, the object focus f1 is exactly formed on the retina 40. The track of the light in this case is shown by reference number 50. However, in some cases, the iris 10 which adjusts the lens 30 excessively contracts and the pupil is enlarged. In that case, as indicated by the dotted line of reference number 60, the external light comes in through wider area than the operated cornea area and, as a result, the focus f2 of the object image is formed in front of the retina 40. Patients who have this phenomena feel glare or halo spread out from the objects when they see the objects. This phenomena may cause troubles and inconveniences. Especially, the patient has a difficulty in driving at night.

Conventionally, an ophthalmologist treats the patient in such a way that the doctor asks the patient some questions about the symptoms and hears the answers. Based on the answer the doctor analyzes the condition of illness and the degree of remedy. For instance, the doctor asks how much glare the patient feels when seeing a street light at night and checks the condition of illness by the answer.

Beyond the above conventional way, the present invention provides an apparatus which can quantitatively analyze the phenomena of glare and the method for the same.

The purpose of the present invention is to provide an apparatus which can quantitatively analyze the phenomena of glare and the method for the same.

Quantitatively analysis method for the phenomena of glare according to the present invention includes the steps of reading light source picture information from a memory part and displaying the light source picture on a display part, reading position information of the circumference of the glare when a patient suffering from the phenomena of glare draws circumference line of the glare by means of a pointing device and calculating area of circumference of glare and outputting the calculated area. The output of the area indicates the condition of illness and the degree of remedy of the patient.

It is preferable that the quantitatively analysis method for the phenomena of glare further includes the step of producing circumference display information by using the position information of the circumference of the glare and displaying circumference on the light source picture on the display part according to the circumference display information. This display visually enhances the understanding of the condition of illness and the degree of remedy. Especially, the step of calculating area of circumference of glare may includes the steps of calculating distances between points of the circumference which are symmetric each other with respect to a central point of the light source, producing average value of the distances and calculating area of circle by using the average distance value as a diameter.

The present invention may be embodied by a computer readable storage medium containing a computer readable program to make computer execute the described above steps.

Quantitatively analysis apparatus for the phenomena of glare according to the present invention includes means for memorizing light source picture information, means for reading the light source picture information and displaying the light source picture on a display part, means for inputting position information of circumference, means for calculating area of the circumference of glare by using the position information of the circumference of glare and means for outputting the calculated area.

Preferably, the quantitatively analysis apparatus for the phenomena of glare further includes means for producing circumference display information by using the position information of the circumference of the glare and means for displaying circumference on the light source picture on the display part according to the circumference display information. Especially, the means for calculating area of circumference of glare may include means for calculating distances between points of the circumference which are symmetric each other with respect to a central point of the light source, means for producing average value of the distances and means for calculating area of circle by using the average distance value as a diameter.

DETAILED EXPLANATION OF PREFERRED EMBODIMENT

Now, the present invention will be described with reference to the accompanying drawings.

Figure 1:
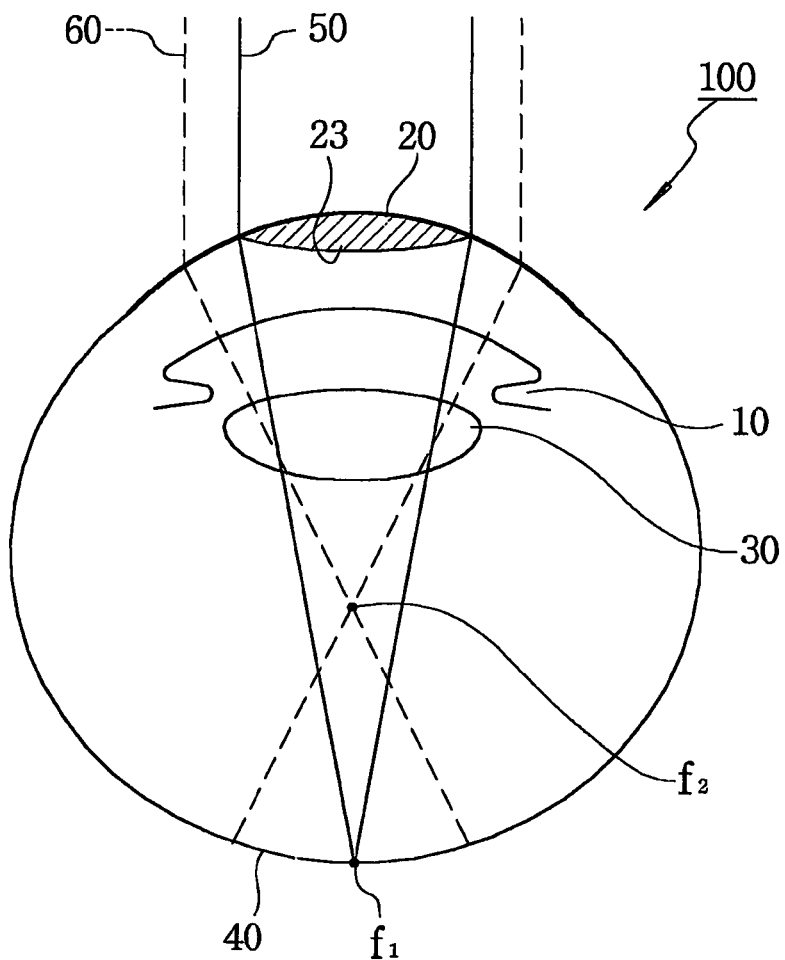
FIG. 1 is a view showing the structure of an eye in which the phenomena of glare occurs.
Figure 2:
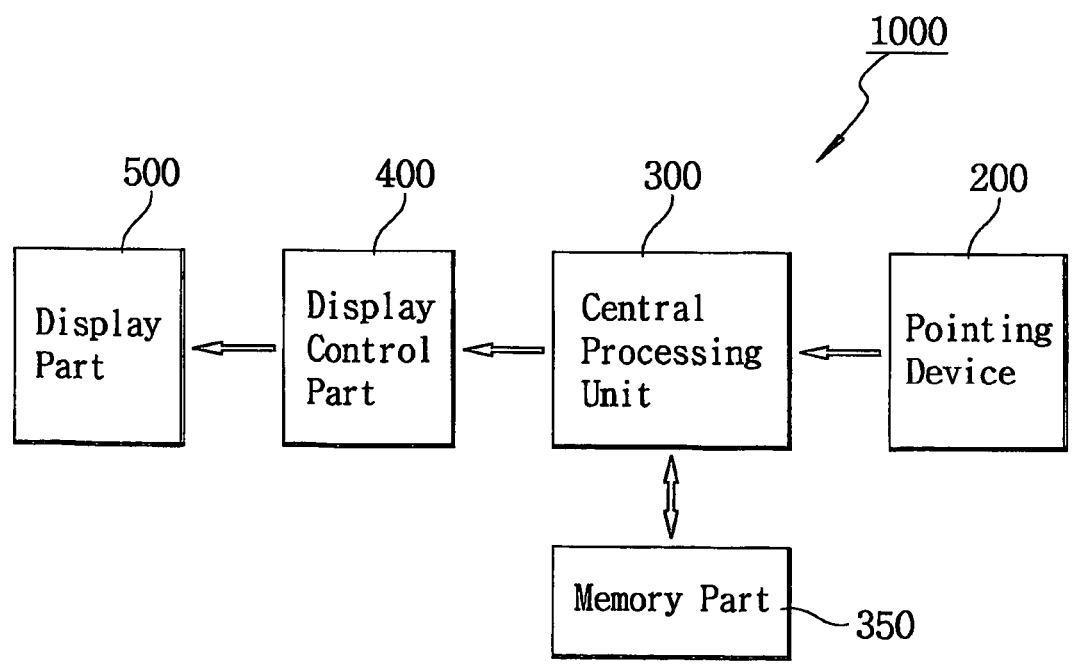
FIG. 2 is a view showing configuration of a quantitative analysis apparatus according to the present invention.

Firstly, with reference to FIG. 2, the quantitative analysis apparatus for phenomena of glare 1000 has a central processing unit 300, a memory part 350 and a pointing device 200. The memory part 350 and the pointing device 200 are coupled with the central processing unit 300, respectively.

Also, the quantitative analysis apparatus for phenomena of glare 1000 has a display control part 400 through which a display part 500 is coupled with the central processing unit 300.

The central processing unit 300 includes microprocessor and the memory part 350 includes RAM or ROM and memorizes a program by which the central processing unit 300 works and data which the central processing unit 300 processes.

The pointing device 200 is a device which can inputs a position information of what a user points. If the user draws line which is straight or curve, the position information of the drawn line is input. A mouse, a track ball, touch pad, light pen or a tablet is an example of the pointing device 200. When a patient suffering from the phenomena of glare sees the display part 500 displaying a light source picture, he or she feels the glare spread out from the light source. The patient draws circumference line of the glare by means of the pointing device 200 and the position information of the circumference of the glare is input to the central processing unit 300.

The display control part 400 receives picture information processed by the central processing unit 300 and controls the display part 400 to display the picture. The graphic card on personal computer(PC) is one example.

The display part 500 is such as CRT, PDP or LCD and displays the picture according to the control of the display control part 400.

Figure 4:
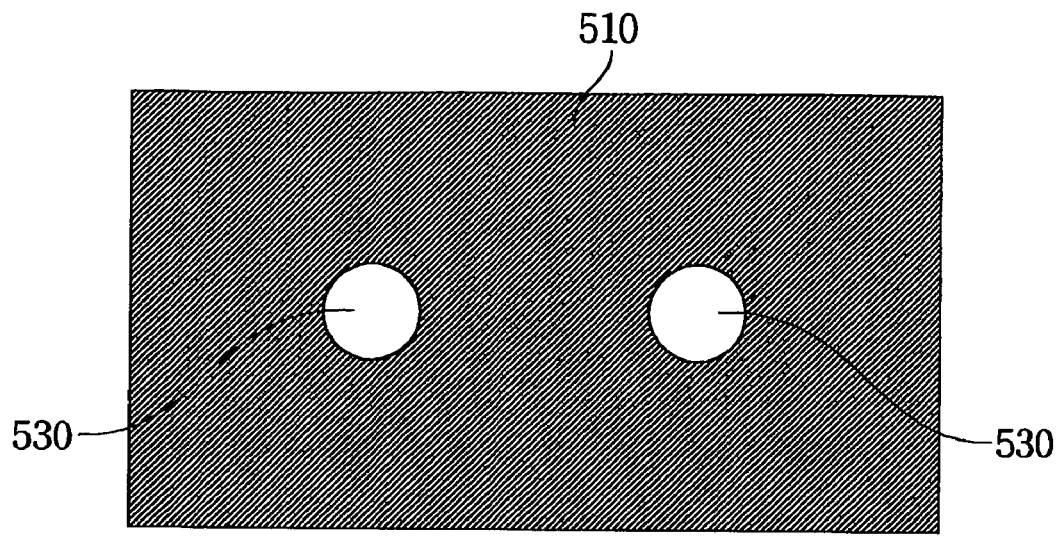
FIG. 4 is a view showing a light source picture displayed on a display part of the present invention.

The memory part 350 memorizes light source picture information. The light source picture is a picture displayed on the display part 500 which exposes a light source. The light source is a part of the picture at which the patient suffering from the phenomena of the glare attentively looks when the patient is treated. For instance, FIG. 4 shows the light source picture formed by two white circles 530 on a black ground 510. The two circles 530 become the light source and the patient is ordered to look at the two circles 530when treated. This embodiment shows the light source formed by the two circles, but it is not limited thereto and the light source can be formed by a circle or another polygon. The light source picture information is directed to such an information by which the display part 500 displays the light source picture. The light source picture information may be a set of values indicating position of points and color thereof or may be vector values indicating a shape of the light source and the related color. The memory part 350 memorizes the light source picture information.

Now, the work of the present invention is explained.

Firstly, the central processing unit 300 reads the light source picture information from the memory part 350. Then, the central processing unit 300 processes the information and prepare light source picture display information and transfers the light source picture display information to the display control part 400. The display control part 400 controls the display part 500 to display the light source picture. Accordingly, the light source picture is displayed on the display part 500, for instance, as shown in FIG. 4.

The patient suffering from the phenomena of glare attentively looks at the light source on the light source picture displayed on the display part 500. A normal person does not feel any glare when he or she looks at the light source 530. However, the patient feels the glare around the light source 530. The patient feeling the glare draws circumference line of the glare by means of the pointing device 200 so that the central processing unit 300 reads the position information of the circumference.

The central processing unit 300 which read the position information of the circumference calculates circumference area which the circumference occupies. Next, the central processing unit 300 outputs the calculated area. As an example, the circumference area of the glare may be directly output to the display part 500 or, alternatively, to a printer.

This output of calculated circumference area indicates the condition of illness of the patient suffering from the phenomena of the glare. For instance, initially, the output of the circumference area was 9 and as treatment progresses the area becomes smaller as 7, 5, 3. By this way, it is possible to express the condition of illness or the degree of remedy by number. Alternatively, the memory part 350 memorizes the calculated circumference area, and the central processing unit 300 reads the circumference area and subtracts the area of the light source 530 from the circumference area, then outputs the result.

The circumference area of the glare may be calculated by various ways. The following shows one example according to the present invention. Calculate distances between points of the circumference which are symmetric each other with respect to a central point of the light source 530 and produce average value of the distances, then calculate area of circle by using the average distance value as a diameter. The area of the circle becomes the circumference area of the glare.

Figure 5:
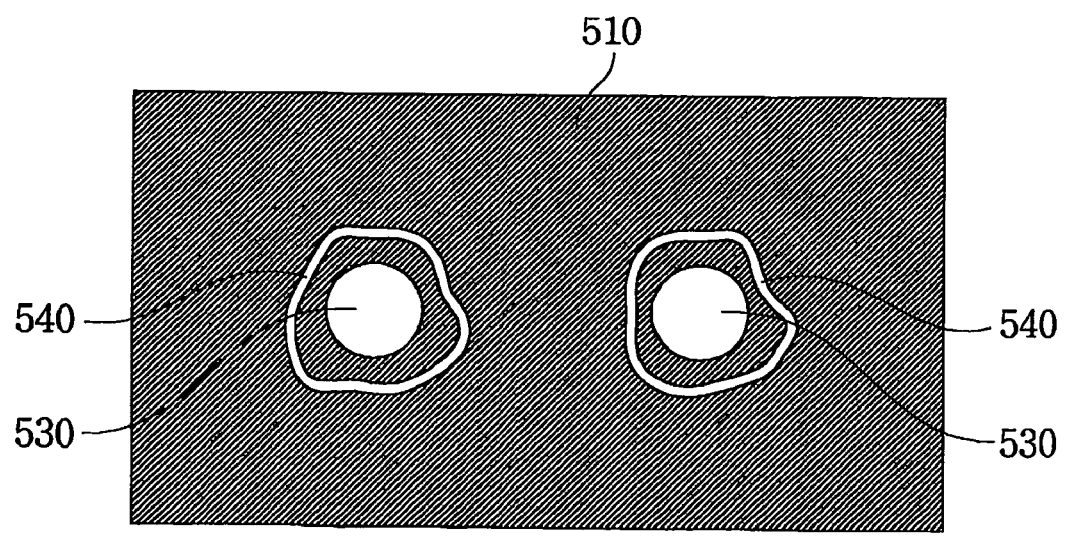
FIG. 5 is a view showing a picture displayed on the display part in which a circumference line of glare around the light source is formed when a patient suffering from the phenomena of glare draws the circumference line of the glare by means of a pointing device.

Preferably, the central processing unit 300 which read the position information of the circumference of the glare processes the position information to produce circumference display information and transfers the circumference display information to the display control part 400 so that the circumference line is displayed on the display part 500. In this case, as shown in FIG. 5, the circumference line of the glare 540 which the patient draws by means of the pointing device 200 is displayed on the light source picture on the display part 500. This display visually enhances the understanding of the condition of illness and the degree of remedy.

Figure 3:
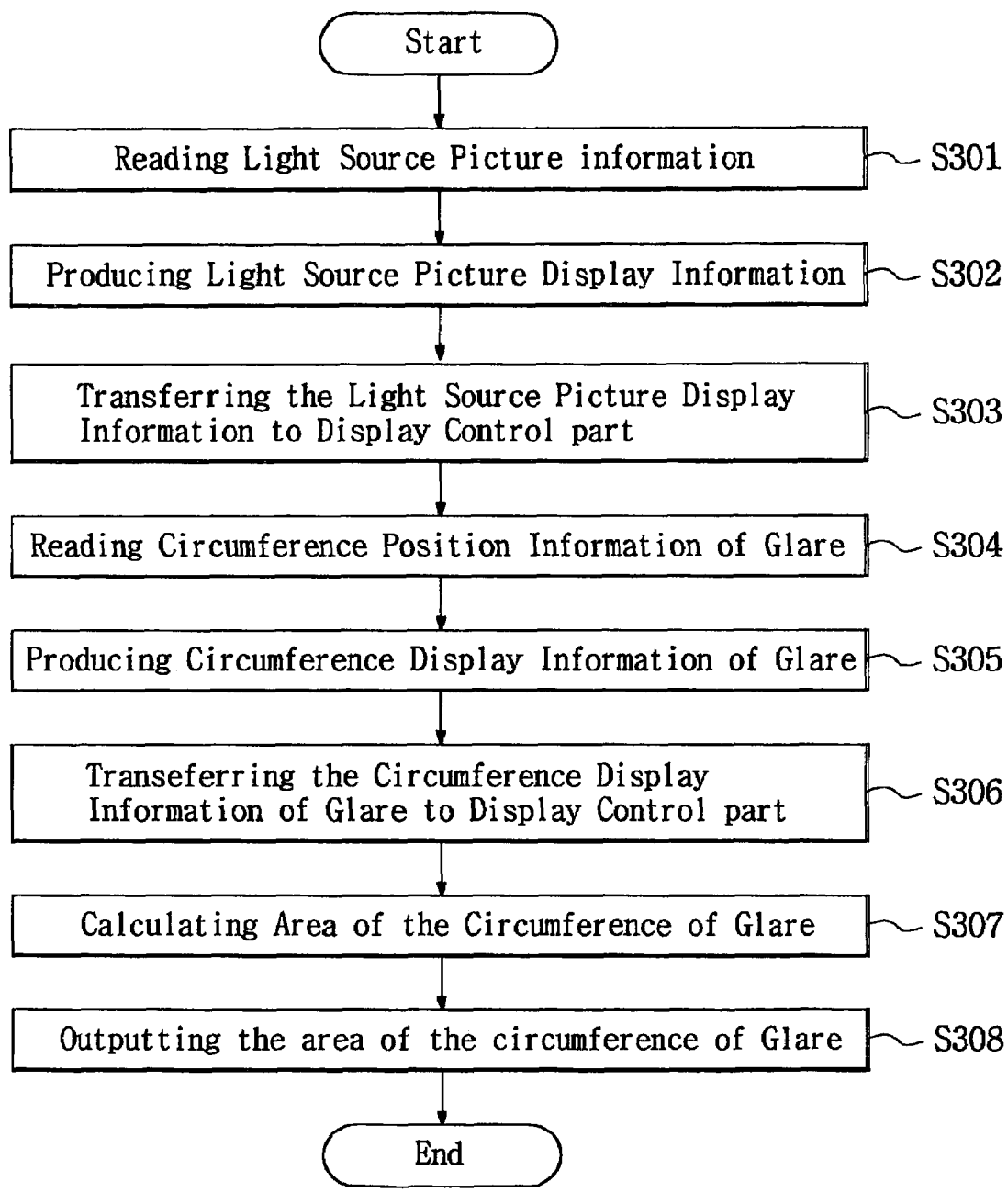
FIG. 3 is a flow chart showing the process of CPU-work of the quantitative analysis apparatus shown in FIG. 2.

The work of the central processing unit 300 is explained with reference to FIG. 3.

Firstly, the central processing unit 300 reads the light source picture information from the memory part 350. (Step S301) Then, the central processing unit 300 produces the light source picture display information (Step S302) and transfers the produced light source picture information to the display control part 400. (Step S303) After that, the patient looks at the light source picture on the display part 500 and inputs the position of the circumference of the glare by means of the pointing device 200. The central processing unit 300 reads the position information. (Step S304) At this time, it is preferable that the central processing unit 300 processes the position information and produces the circumference display information (Step S305), and transfers the circumference display information to the display control part 400 (Step S306) so that the circumference line is displayed with respect to the light source 530 on the display part 500.

The central processing unit 300 calculates the area of the circumference of the glare from the position information of the circumference (Step S307), and outputs the area. (Step S308) In the present invention, it is possible to adjust the size of the light source 530 on the light source picture. In this case, an input device such as a key board (not shown) is coupled to the central processing unit 300. At this time, central processing unit 300 includes means for adjusting the size of the light source. The central processing unit 300 adjusts the size of the light source according to the input of the keyboard, produces the light source picture display information and transfers it to the display control part 400.

The present invention may be embodied by computer readable codes on a computer readable storage medium. For instance, the computer readable storage medium includes ROM, RAM, CD-ROM, magnetic tape, floppy disk or optical disk. Further, the present invention may be embodied by carrier wave(for example, the transmission by Internet). The computer readable storage medium can be distributed to computers connected to each other by network and the present invention can be executed in distributable way.

INDUSTRIAL APPLICABILITY

As described above, the present invention displays the light source picture on the display part, calculates the area of circumference line which the patient suffering from the phenomena of glare draws by means of the pointing device and outputs the area. The output area indicates the condition of illness or the degree of remedy. Therefore, the opthalmologist can quantitatively analyze a condition of the illness and the degree of remedy of the phenomena of glare.

Accordingly, it is understood that the purpose of the present invention is accomplished. The present invention is described with reference to the specific embodiments, but the invention is not limited there to. Only the following claims will determine the scope of the invention.

What is claimed is:

1. A method for quantitative analysis of glare comprising the steps of:
    (a) displaying a light source on a display;
    (b) reading from the display position information for a line drawn on the display by an observer using a pointing device, the line indicating glare from the light source;
    (c) calculating an area of the glare; and
    (d) outputting the calculated area.

2. The method of claim 1 wherein the line is a circumferential line drawn on the display about the light source.

3. The method for the quantitative analysis of glare as set forth in claim 2 further comprising the steps of:
    (a) producing circumference display information by using the position information; and
    (b) displaying a circumference on the display according to the circumference display information.

4. The method for the quantitative analysis of glare as set forth in claim 2 wherein the step of calculating the area of the glare comprises:
    (a) calculating distances between points of the circumferential line which are symmetric with respect to a central point of the light source;
    (b) producing an average value of the distances; and
    (c) calculating the area of a circle by using the average distance value as a diameter.

5. The method of claim 1 wherein the display is a computer driven display and the display of the light source is generated from data stored in a computer memory.

6. An apparatus for the quantitative analysis of glare comprising:
    a) a display for displaying a light source;
    b) an input for drawing a line on the display that indicates glare from the light source;
    c) a computer connected to the display and the input for calculating an area of the glare by using position information for the line; and
    d) an output for outputting the calculated area.

7. The apparatus of claim 6 wherein the line is a circumferential line drawn on the display about the light source.

8. The apparatus of claim 7 wherein circumference display information is produced by using position information for the line and a circumference is displayed on the display according to the circumference display information.

9. The apparatus for the quantitative analysis of glare as set forth in claim 7 wherein the computer for calculating area of glare calculates distances between points on the circumferential line which are symmetric with respect to a central point of the light source, determines an average value of the distances and calculates an area of a circle by using the average distance value as a diameter.

10. The apparatus of claim 6 wherein the display is a computer driven display and the display of the light source is generated from data stored in a computer memory.

11. A computer readable storage medium containing a computer readable program for performing the steps of
    (a) displaying a light source on a display;
    (b) reading from the display position information for a line drawn on the display by an observer using a pointing device, the line indicating glare from the light source;
    (c) calculating an area of the glare; and
    (d) outputting the calculated area.

12. The computer readable storage medium of claim 11 wherein the line is a circumferential line drawn on the display about the light source further containing a computer readable program for performing the steps of
    (a) producing circumference display information by using the position information; and
    (b) displaying a circumference on the display according to the circumference display information.

13. The computer readable storage medium of claim 11 wherein the line is a circumferential line drawn on the display about the light source further containing a computer readable program for performing the steps of
    (a) calculating distances between points on the circumferential line which are symmetric with respect to a central point of the light source;
    (b) producing an average value of the distances; and
    (c) calculating the area of a circle by using the average distance value as a diameter.

14. An apparatus for the quantitative analysis of glare comprising:
    (a) means for displaying an image of a light source on a display;
    (b) means for drawing a line on the display indicating glare from the light source;
    (c) means for calculating area of glare by using position information describing the line; and
    (d) means for outputting the calculated area.

15. The apparatus of claim 14 wherein the line is a circumferential line drawn on the display about the image of the light source.

16. The apparatus for the quantitative analysis of glare of claim 15 further comprising:
    (a) means for producing circumference display information by using the position information; and
    (b) means for displaying a circumference on the display according to the circumference display information.

17. The apparatus for the quantitative analysis of glare of claim 15 wherein the means for calculating area of glare comprises:
    (a) means for calculating distances between points on the circumferential line which are symmetric with respect to a central point of the light source;
    (b) means for producing an average value of the distances; and
    (c) means for calculating area of circle by using the average distance value as a diameter.

18. The apparatus of claim 14 further comprising means for storing the image of a light source.

* * * * *